(12) United States Patent
Trotter et al.

(10) Patent No.: US 12,270,750 B2
(45) Date of Patent: *Apr. 8, 2025

(54) ADAPTIVE SORTING FOR PARTICLE ANALYZERS

(71) Applicant: Becton, Dickinson and Company, Franklin Lakes, NJ (US)

(72) Inventors: Joseph T. Trotter, La Jolla, CA (US); Keegan Owsley, Campbell, CA (US); Jonathan Lin, San Gabriel, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/641,039

(22) Filed: Apr. 19, 2024

(65) Prior Publication Data

US 2024/0344964 A1 Oct. 17, 2024

Related U.S. Application Data

(63) Continuation of application No. 18/130,571, filed on Apr. 4, 2023, now Pat. No. 11,994,459, which is a
(Continued)

(51) Int. Cl.
| | | |
|---|---|---|
| *G01N 15/14* | (2024.01) | |
| *B07C 5/342* | (2006.01) | |
| *B07C 5/36* | (2006.01) | |
| *G01N 15/1434* | (2024.01) | |
| *G01N 15/149* | (2024.01) | |

(Continued)

(52) U.S. Cl.
CPC ....... *G01N 15/1459* (2013.01); *B07C 5/3425* (2013.01); *B07C 5/361* (2013.01); *G01N 15/1425* (2013.01); *G01N 15/1434* (2013.01); *G06V 10/87* (2022.01); *G06V 20/695* (2022.01);
(Continued)

(58) Field of Classification Search
CPC ............. G01N 15/149; G01N 15/1459; G01N 15/1434; G01N 15/1425; G16C 20/00; G16C 20/30; G16C 20/40; G16C 20/50; G16C 20/70; G16C 20/80; G16C 20/90
See application file for complete search history.

(56) References Cited

U.S. PATENT DOCUMENTS

| | | |
|---|---|---|
| 8,290,625 B2 | 10/2012 | Degeal et al. |
| 9,934,364 B1 | 4/2018 | Kumar et al. |

(Continued)

FOREIGN PATENT DOCUMENTS

| | | |
|---|---|---|
| CN | 102177427 A | 9/2011 |
| CN | 102279146 A | 12/2011 |

(Continued)

OTHER PUBLICATIONS

Lo, et al. "Automated gating of flow cytometry data via robust model-based clustering", Cytometry A. Apr. 2008;73(4):321-32.

*Primary Examiner* — Michael McCullough
*Assistant Examiner* — Jessica L Burkman
(74) *Attorney, Agent, or Firm* — Bret E. Field; BOZICEVIC, FIELD & FRANCIS LLP

(57) ABSTRACT

A cell sorting system that automatically generates a sorting strategy based on examples of target events provided by an operator. The target events can be selected using measurements ranging from traditional flow cytometry measurements to derived measurements that are computationally expensive to complex measurements such as images.

16 Claims, 6 Drawing Sheets

Related U.S. Application Data continuation of application No. 17/545,325, filed on Dec. 8, 2021, now Pat. No. 11,644,407, which is a continuation of application No. 16/596,428, filed on Oct. 8, 2019, now Pat. No. 11,227,672.

(60) Provisional application No. 62/747,004, filed on Oct. 17, 2018.

(51) Int. Cl.
*G06V 10/70* (2022.01)
*G06V 20/69* (2022.01)
*G16C 20/20* (2019.01)

(52) U.S. Cl.
CPC ........... *G06V 20/698* (2022.01); *G16C 20/20* (2019.02); *G01N 15/149* (2024.01)

(56) References Cited

U.S. PATENT DOCUMENTS

| | | |
|---|---|---|
| 10,616,219 B2 | 4/2020 | Stadnisky |
| 2003/0078703 A1 | 4/2003 | Potts et al. |
| 2009/0287356 A1 | 11/2009 | Dunne |
| 2009/0289356 A1 | 11/2009 | Camacho et al. |
| 2012/0244610 A1 | 9/2012 | Durack et al. |
| 2014/0309782 A1 | 10/2014 | Sharpe et al. |
| 2015/0268244 A1 | 9/2015 | Cho et al. |
| 2015/0276576 A1 | 10/2015 | Sharpe et al. |
| 2017/0350804 A1 | 12/2017 | Ye et al. |
| 2018/0095022 A1 | 4/2018 | Petersen |
| 2021/0005287 A1 | 1/2021 | Fuentes et al. |

FOREIGN PATENT DOCUMENTS

| | | |
|---|---|---|
| EP | 3372985 A1 | 9/2018 |
| JP | 2018503801 A | 2/2018 |
| JP | 2018505392 A | 2/2018 |
| WO | WO2014121126 A2 | 8/2014 |
| WO | WO2015168774 A1 | 5/2015 |
| WO | WO2017214572 A1 | 12/2017 |

ADAPTIVE SORTING FOR PARTICLE ANALYZERS

BACKGROUND

Technical Field

This disclosure relates to relates generally to the field of automated particle assessment, and more particularly to sample analysis and particle characterization methods.

Background

Particle analyzers, such as flow and scanning cytometers, are analytical tools that enable the characterization of particles on the basis of electro-optical measurements such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one or more for each of the distinct dyes to be detected are included in the analyzer. For example, some embodiments include spectral configurations where more than one sensor or detector is used per dye. The data obtained comprise the signals measured for each of the light scatter detectors and the fluorescence emissions.

Particle analyzers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured features. The use of standard file formats, such as an "FCS" file format, for storing data from a particle analyzer facilitates analyzing data using separate programs and/or machines. Using current analysis methods, the data typically are displayed in 1-dimensional histograms or 2-dimensional (2D) plots for ease of visualization, but other methods may be used to visualize multidimensional data.

The parameters measured using, for example, a flow cytometer typically include light at the excitation wavelength scattered by the particle in a narrow angle along a mostly forward direction, referred to as forward scatter (FSC), the excitation light that is scattered by the particle in an orthogonal direction to the excitation laser, referred to as side scatter (SSC), and the light emitted from fluorescent molecules in one or more detectors that measure signal over a range of spectral wavelengths, or by the fluorescent dye that is primarily detected in that specific detector or array of detectors. Different cell types can be identified by their light scatter characteristics and fluorescence emissions resulting from labeling various cell proteins or other constituents with fluorescent dye-labeled antibodies or other fluorescent probes.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multi-dimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; and 6,944,338; and U.S. Pat. Pub. No. 2012/0245889, each incorporated herein by reference.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to characterize and produce a diagnostic profile of a population of biological particles.

Isolation of biological particles has been achieved by adding a sorting or collection capability to flow cytometers. Particles in a segregated stream, detected as having one or more desired characteristics, are individually isolated from the sample stream by mechanical or electrical separation. This method of flow sorting has been used to sort cells of different types, to separate sperm bearing X and Y chromosomes for animal breeding, to sort chromosomes for genetic analysis, and to isolate particular organisms from complex biological population.

Gating is used to classify and help make sense of the large quantity of data that may be generated from a sample. Given the large quantities of data presented for a given sample, there exists a need to efficiently control the graphical display of the data.

Fluorescence-activated particle sorting or cell sorting is a specialized type of flow cytometry. It provides a method for sorting a heterogeneous mixture of particles into one or more containers, one cell at a time, based upon the specific light scattering and fluorescent characteristics of each cell. It records fluorescent signals from individual cells, and physically separates cells of particular interest. The acronym FACS is trademarked and owned by Becton Dickinson and may be used to refer to devices for performing fluorescence-activated particle sorting or cell sorting.

The particle suspension is placed near the center of a narrow, rapidly flowing stream of liquid. The flow is arranged so that on the average there is a large separation between particles relative to their diameter as they arrive stochastically (Poisson process) into the detection region. A vibrating mechanism causes the emerging fluid stream to break off in a stable manner into individual droplets that contain particles previously characterized in the detection region. The system is generally adjusted so that there is a low probability of more than one particle being in a droplet. If a particle is classified to be collected, a charge is applied to the flow cell and emerging stream during the period of time one or more drops form and break off from the stream. These charged droplets then move through an electrostatic deflection system that diverts droplets into target containers based upon the charge applied to the droplet.

A sample can include thousands if not millions of cells. Cells may be sorted to purify a sample to the cells of interest. The sorting process can generally identify three varieties of cells: cells of interest, cells which are not of interest, and cells which cannot be identified. In order to sort cells with high purity (e.g., high concentration of cells of interest), droplet generating cell sorters typically abort the sort electronically if the desired cells are too close to another unwanted cell and thereby reduce contamination of the sorted populations by any inadvertent inclusion of an unwanted particle within the droplet containing the particle of interest.

SUMMARY

In one innovative aspect, a computer-implemented method is provided. The method is performed under control of one or more processing devices. The method includes receiving, from a communication device, a reference sorting criteria for a sample with a particle analyzer. The method includes identifying candidate event classifiers for the sample based at least in part on the reference sorting criteria and the sample. The method includes generating a sorting strategy, the sorting strategy including at least one event classifier from the candidate event classifiers. The method includes generating a metric indicating an accuracy of the sorting strategy. The method includes determining that the metric meets or exceeds a minimum accuracy threshold for the sample. The method includes configuring the particle analyzer to classify a particle for the sample based at least in part on a multidimensional measurement for the particle and a sorting strategy.

In some implementations, the reference sorting criteria may include gate information identifying a range of measurements for classifying the particle. In some implementations, the reference sorting criteria may include an image showing a reference particle to be collected from the sample.

The method may also include transmitting a sorter configuration to the particle analyzer, wherein the sorter configuration represents the sorting strategy; and adjusting sorting circuitry based at least in part on the sorter configuration. An example of the sorting circuitry is a field programmable gate array.

In some implementations, the multidimensional measurement received from the particle analyzer may include a measurement of light emitted fluorescently by the particle. The light emitted fluorescently by the particle may include light emitted fluorescently by antibodies bound to the particle.

In some implementations, the metric may include an f-measure of the sorting strategy. A precision component of the f-measure represents purity for sorting of the sample according to the sorting strategy. A recall component of the f-measure represents yield for sorting of the sample according to the sorting strategy.

Some implementations of the method may include storing, in a data store, the candidate event classifiers, wherein the candidate event classifiers comprise at least two of: (a) a computational sorting classifier including: a scoring and relevant target or off-target score, (b) a score for a particle measurement is compared with the relevant target or off-target score for sorting; (c) a transformation to convert one or more measurements for a particle into an approximate measurement for the particle; (d) a parameter projection to convert a population represented by the reference sorting criteria from a first parameter space that is not sortable into a second parameter space that can be sorted; and (e) a feature extraction to generate a vector features from images or high-dimensional measurements, wherein the vector of features are used to classify a particle.

The method may include receiving, from the particle analyzer, a hardware identifier indicating sorting circuitry implemented in the particle analyzer. In such implementations, identifying the candidate event classifiers may be further based at least in part on the hardware identifier.

In another innovative aspect, a system is provided. The system includes one or more processing devices and a computer-readable storage medium comprising instructions. The instructions, when executed by the one or more processing devices, cause the system to receive, from a communication device, a reference sorting criteria for a sample with a particle analyzer; identify candidate event classifiers for the sample based at least in part on the reference sorting criteria and the sample; generate a sorting strategy, the sorting strategy including at least one event classifier from the candidate event classifiers; generate a metric indicating an accuracy of the sorting strategy; determine that the metric meets or exceeds a minimum accuracy threshold for the sample; generate a control signal to adjust an operational state for an analytical means included in the particle analyzer, wherein the operational state reflects the sorting strategy; and transmit the control signal to the analytical means to achieve the operational state.

The analytical means may include sorting electronics communicatively coupled to a deflection plate. The particle analyzer may be configured to identify a target vessel for a particle based at least in part on a measurement corresponding the sorting strategy for the target vessel. Adjusting the operational state may include application of a charge via a deflector plate to direct the particle into a target vessel.

The analytical means may include a fluidics system, and adjusting the operational state may include regulating a pressure applied during an experiment for analyzing the sample.

DETAILED DESCRIPTION

Figure 1:
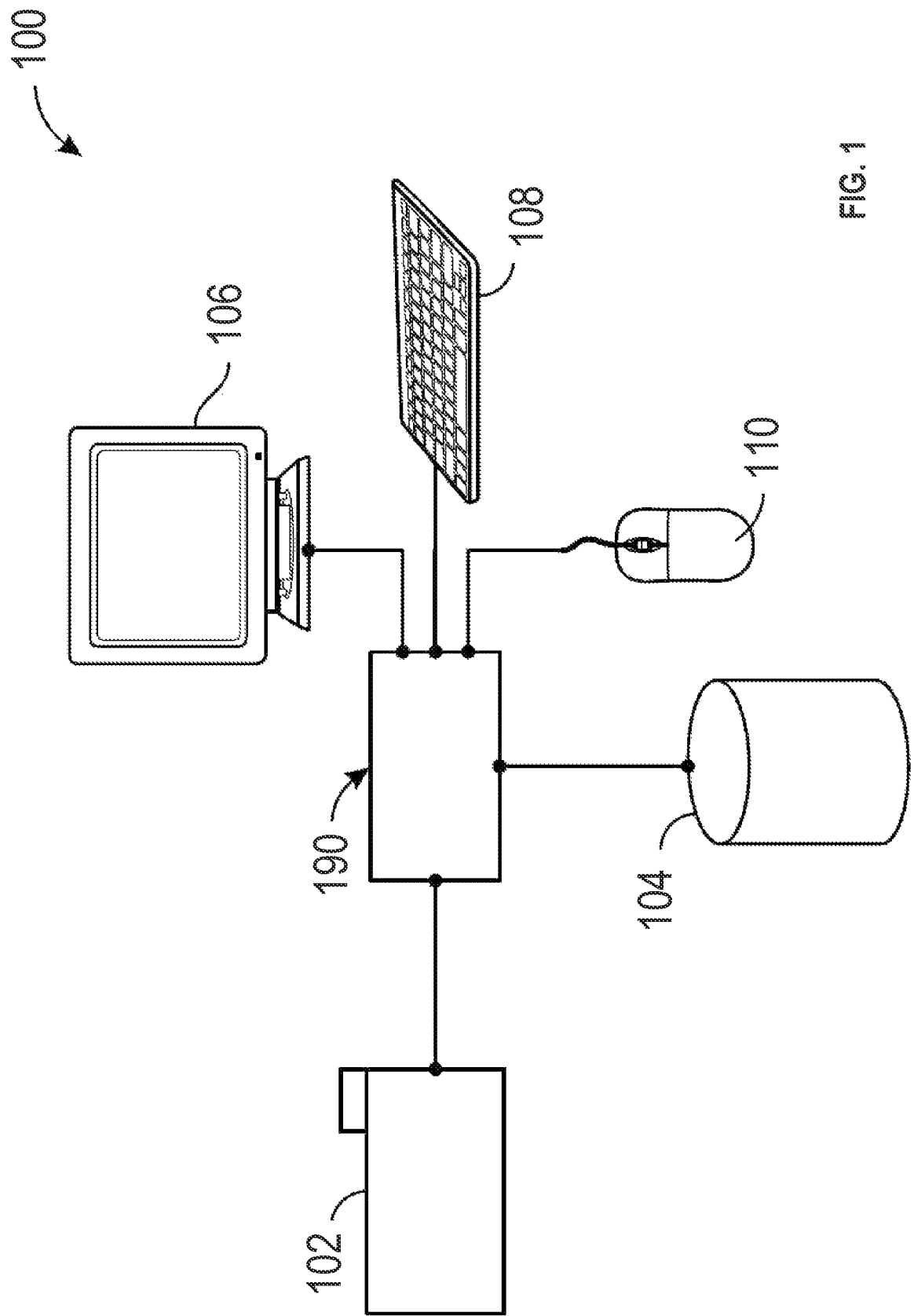
FIG. 1 shows a functional block diagram for one example of a transformation control system for analyzing and displaying biological events.

Features are described for a particle sorter that automatically develops a sorting strategy based on target event populations selected by the user. A user may select one or more target populations based on measurements including traditional flow measurements and non-traditional parameters such as images and image features. The system then converts the target population into a sorting strategy and configures the sort hardware accordingly.

Using the user selection to guide selection of an optimized classifier for sorting addresses several issues with user defined classifiers. One issue relates to the difficulty in drawing gates in high-dimensional data spaces. Computing systems may render two or three dimensions of data simultaneously such as via a plot. A user may select an area of the plot to identify a population of interest. However, as the number of dimensions grows beyond three, the ability to visualize and accurately draw a gate for the population of interest becomes difficult if not impossible using existing technology. Furthermore, even when a given plot can be used for selecting a population, a gate truly reflecting the population of interest may be highly complex. For example, the gate may be represented using asymmetric, multi-vertex shapes in high-dimensional spaces.

Another issue relates to hindsight bias in selecting new populations of interest. The set of events may relate to complex biological systems. A user's ability to select may be influenced by prior experience and training. However, that training may not include specific knowledge of a parameter that may improve the sorting strategy. Furthermore, users may find it too difficult to develop gating strategies based on large numbers of parameters.

Another issue relates to the ability to distinguish events using existing technologies. Because the gating relies on graphic representations of events, in some instances, a user may not be able to quantify differences between events. It may be difficult to quantify what a cell "looks like" based on the two or three dimensional plots. Furthermore, a population of interest may inadvertently include subpopulations that are undesirable, but hidden amongst the events actually desired.

A further issue relates to the fidelity available to select events of interest. In some instances, sortable parameters that quantify differences to distinguish events may not be represented in the event data to the user. In some cases, a composite or transformed parameter may better serve to characterize the events of interest. As another example, parameters that describe the appearance of a cell may be computationally expensive or difficult to use for sorting.

To address these and other issues with generating sort configurations, a two-phase classification process is described. First, a user may define target populations using combinations one or more existing methods such as gating on traditional flow cytometry parameters (e.g., pulse area, width, and height), gating on computationally difficult parameters (e.g., parameters that are difficult or impossible to compute on commercially available hardware within the latency required for droplet sorting such as image based parameter (e.g., spot counting, object perimeter, etc.)), gating on non-parametric transformations of data (e.g., gating on results of dimensionality reduction algorithms such as t-SNE or Verity CEN-SE™), providing example events (e.g., sort events similar to the example event(s) provided), or providing example images (e.g., sort events that look similar to the example image(s)).

During the second phase, the system optimizes the sorting for the user-defined target populations by selection and application of an optimized sorting strategy. The strategy may include automatically detecting populations and scoring each event against relevant target and off-target populations (computational sort). The strategy may include approximation of transforms (non-parametric and parametric) using neural networks or other machine learning techniques. The strategy may include projecting target populations from a parameter space that is not sortable to one that is. As part of projecting the target populations, the system may identify computable parameters that, in combination, approximate parameters that are not easily computable. The strategy may include automatically extracting features from images or high-dimensional measurements including, for example, time series waveform data. One example of the automatic feature extraction is an auto-encoder neural network to learn relevant image features to be used in sorting decisions.

Candidate classifiers may be assessed based on an expected purity or expected sorting yield for the classification. For example, the classification may provide statistical confidence in how accurate the population may be sorted. This confidence may be used to approximate how pure the sorted sample will be (e.g., how much of the sorted material will be the population of interest). Performance of classification algorithms can be characterized using two metrics: precision and recall. Precision is the proportion of positive results that true positives. Recall is the proportion of true positives that were detected as positive. It can be inefficient to maintain multiple metrics of performance. A summary metric (e.g., f-measure) that combines both precision and recall, may be used for increase efficiency and resource utilization of the classification device(s). For example, candidate classification strategies may be compared by computing an f-measure for each candidate using a set of example data. These f-measures can be used to identify the highest performing candidate.

Once an optimized sorting configuration is generated, sorting electronics may receive the configuration and adjust operation to sort a sample accordingly. Because the capabilities of sorting electronics may differ, the system may generate the sorting strategy based in part on the target sorting electronics. This ensures that the optimally generated configuration can be applied on the target sorting electronics. For example, a strategy may include transforming event data. Some sorting electronics may not be capable of performing certain mathematical operations required for the transformation. In such instances, the set of candidate classifiers may exclude the transformation when a sort configuration is requested for the limited sorting electronics.

As used herein, the terms set forth with particularity below have the following definitions. If not otherwise defined in this section, all terms used herein have the meaning commonly understood by a person skilled in the arts to which this invention belongs.

As used herein, "system," "instrument," "apparatus," and "device" generally encompass both the hardware (e.g., mechanical and electronic) and, in some implementations, associated software (e.g., specialized computer programs for graphics control) components.

As used herein, an "event" or "event data" generally refers to the packet of data measured from a single particle, such as cells or synthetic particles. Typically, the data measured from a single particle include a number of physical measurements, including one or more physical measurements from detectors measuring light scatter, and at least one parameter or feature derived from fluorescence detected from the particle such as the intensity of the fluorescence. Thus, each event is represented as a vector of measurements and features, wherein each measured parameter or feature corresponds to one dimension of the data space. In some embodiments, the data measured from a single particle include image, electric, temporal, or acoustic data. An event may be associated with an experiment, an assay, or a sample source which may be identified in association with the measurement data.

As used herein, a "population", or "subpopulation" of particles, such as cells or other particles, generally refers to a group of particles that possess properties (for example, optical, impedance, or temporal properties) with respect to one or more measured parameters such that measured parameter data form a cluster in the data space. Thus, populations are recognized as clusters in or regions of density in the data. Conversely, each data cluster generally is interpreted as corresponding to a population of a particular type of cell or particle, although clusters that correspond to noise or background typically also are observed. A cluster may be defined in a subset of the dimensions, e.g., with respect to a subset of the measured parameters, which corresponds to populations that differ in only a subset of the measured parameters or features extracted from the measurements of the cell or particle.

As used herein, a "gate" generally refers to a classifier boundary identifying a subset of data of interest. In cytometry, a gate may bound a group of events of particular interest. As used herein, "gating" generally refers to the process of classifying the data using a defined gate for a given set of data, where the gate may be one or more regions of interest combined with Boolean logic.

As used herein, an "event" generally refers to the assembled packet of data measured from a single particle, such as cells or synthetic particles). Typically, the data measured from a single particle include a number of parameters or features, including one or more light scattering parameters or features, and at least one other parameter or feature derived from measured fluorescence. Thus, each event is represented as a vector of parameter and feature measurements, wherein each measured parameter or feature corresponds to one dimension of the data space.

As used herein "neural networks" or "neural network models" can be conceptualized as networks of nodes. The nodes may be organized into layers where the first layer is an input layer that data flows into. The neural network may also include an output layer where transformed data flows out. Each individual node may have multiple inputs and a single output (e.g., input layer nodes only have a single input). The output of a node represents a linear combination of the inputs. In other words, inputs may be multiplied by an associated constant. The products may be accumulated along a path of nodes with a constant offset. The constant offset, or "bias," may represent another degree of freedom that can be adjusted during the training process. For example, in the context of neural network models based on re-lu, the constant offset may be a threshold since it has the ability to reduce a node value below zero, causing the activation function to output zero.

The resulting value is evaluated using an activation function and the resulting value is used as the output of the node. The nodes in a given layer within the neural network are connected to each node of an adjacent layer. Neural networks may be trained by minimizing the error of the network using gradient descent algorithm and an error function to compare the desired output of the network and the networks actual output. The weighting for one or more nodes may be adjusted to model a desired result produced by the network.

Specific examples of various embodiments and systems in which they are implemented are described further below.

FIG. 1 shows a functional block diagram for one example of an adaptive sorting control system for analyzing and displaying biological events. An analytics controller 190 may be configured to implement a variety of processes for controlling graphic display of biological events.

A particle analyzer 102 may be configured to acquire biological event data. For example, a flow cytometer may generate flow cytometric event data. The particle analyzer 102 may be configured to provide biological event data to the analytics controller 190. A data communication channel may be included between the particle analyzer 102 and the analytics controller 190. The biological event data may be provided to the analytics controller 190 via the data communication channel.

The analytics controller 190 may be configured to receive biological event data from the particle analyzer 102. The biological event data received from the particle analyzer 102 may include flow cytometric event data. The analytics controller 190 may be configured to provide a graphical display including a first plot of biological event data to a display device 106. The analytics controller 190 may be further configured to render a region of interest as a gate around a population of biological event data shown by the display device 106, overlaid upon the first plot. In some embodiments, the gate may be a logical combination of one or more graphical regions of interest drawn upon a single parameter histogram or bivariate plot.

The analytics controller 190 may be further configured to display the biological event data on the display device 106 within the gate differently from other events in the biological event data outside of the gate. For example, the analytics controller 190 may be configured to render the color of biological event data contained within the gate to be distinct from the color of biological event data outside of the gate. The display device 106 may be implemented as a monitor, a tablet computer, a smartphone, or other electronic device configured to present graphical interfaces.

The analytics controller 190 may be configured to receive a gate selection signal identifying the gate from a first input device. For example, the first input device may be implemented as a mouse 110. The mouse 110 may initiate a gate selection signal to the analytics controller 190 identifying the gate to be displayed on or manipulated via the display device 106 (e.g., by clicking on or in the desired gate when the cursor is positioned there). In some implementations, the first device may be implemented as the keyboard 108 or other means for providing an input signal to the analytics controller 190 such as a touchscreen, a stylus, an optical detector, or a voice recognition system. Some input devices may include multiple inputting functions. In such implementations, the inputting functions may each be considered an input device. For example, as shown in FIG. 1, the mouse 110 may include a right mouse button and a left mouse button, each of which may generate a triggering event.

The triggering event may cause the analytics controller 190 to alter the manner in which the data is displayed, which portions of the data is actually displayed on the display device 106, or provide input to further processing such as selection of a population of interest for particle sorting.

In some embodiments, the analytics controller 190 may be configured to detect when gate selection is initiated by the mouse 110. The analytics controller 190 may be further configured to automatically modify plot visualization to optimally facilitate the gating process. The modification may be based on the specific distribution of biological event data received by the analytics controller 190.

The analytics controller 190 may be connected to a storage device 104. The storage device 104 may be configured to receive and store biological event data from the analytics controller 190. The storage device 104 may also be configured to receive and store flow cytometric event data from the analytics controller 190. The storage device 104 may be further configured to allow retrieval of biological event data, such as flow cytometric event data, by the analytics controller 190.

A display device 106 may be configured to receive display data from the analytics controller 190. The display data may comprise plots of biological event data and gates outlining sections of the plots. The display device 106 may be further configured to alter the information presented according to input received from the analytics controller 190 in conjunction with input from the particle analyzer 102, the storage device 104, the keyboard 108, and/or the mouse 110.

In some implementations the analytics controller 190 may generate a user interface to receive example events for sorting. For example, the user interface may include a control for receiving example events or example images. The example events or images or an example gate may be provided prior to collection of event data for a sample, or based on an initial set of events for a portion of the sample.

A common flow sorting technique which may be referred to as "electrostatic cell sorting," utilizes droplet sorting in which a stream or moving fluid column containing linearly segregated particles is broken into drops and the drops containing particles of interest are electrically charged and deflected into a collection tube by passage through an electric field. Current drop sorting systems are capable of forming drops at a rate of 100,000 drops/second in a fluid stream that is passed through a nozzle having a diameter less than 100 micrometers. Droplet sorting typically requires that the drops break off from the stream at a fixed distance from the nozzle tip. The distance is normally on the order of a few millimeters from the nozzle tip and can be stabilized and maintained for an unperturbed fluid stream by oscillating the nozzle tip at a predefined frequency with an amplitude to hold the break-off constant. For example, in some embodiments, adjusting amplitude of a sine wave shaped voltage pulse at a given frequency holds the break-off stable and constant.

Typically, the linearly entrained particles in the stream are characterized as they pass through an observation point situated within a flow cell or cuvette, or just below the nozzle tip. Once a particle is identified as meeting one or more desired criteria, the time at which it will reach the drop break-off point and break from the stream in a drop can be predicted. Ideally, a brief charge is applied to the fluid stream just before the drop containing the selected particle breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Figure 2A:
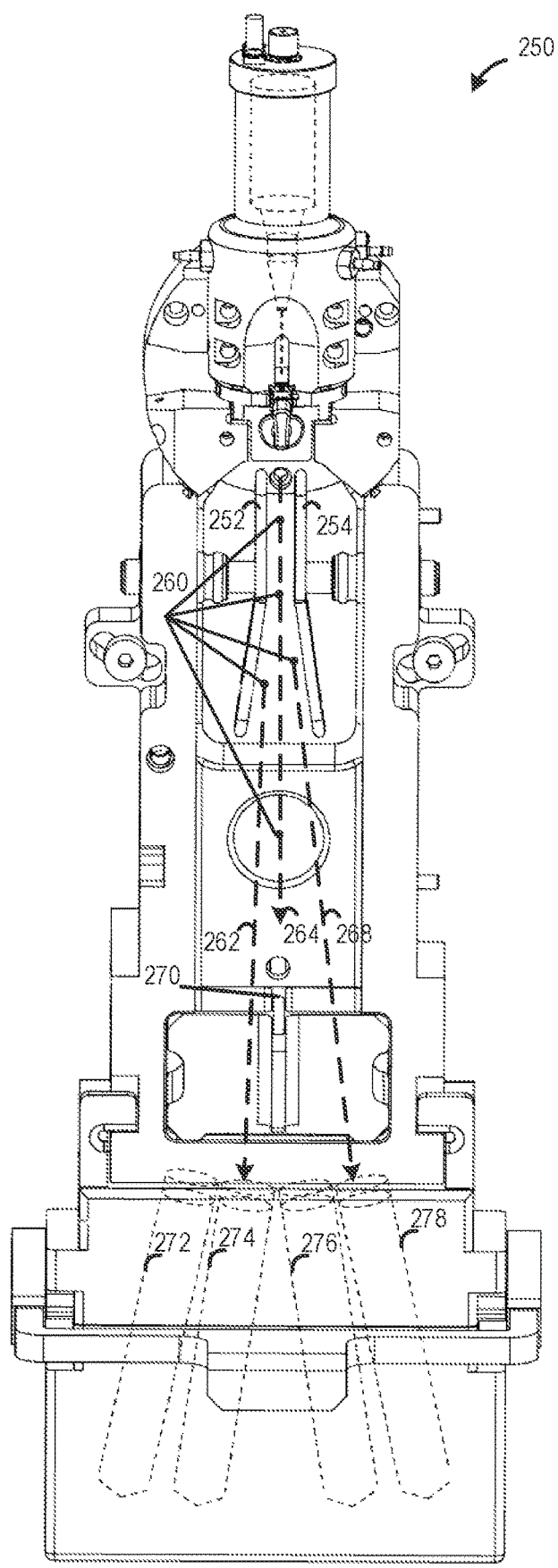
FIG. 2A is a schematic drawing of a particle sorter system, in accordance with one embodiment presented herein.

FIG. 2A is a schematic drawing of a particle sorter system, in accordance with one embodiment presented herein. The particle sorter system 250 shown in FIG. 2A, includes deflection plates 252 and 254. A charge is applied via a stream-charging wire in a barb 256. This creates a stream of particles 260 for analysis. The particles may be illuminated with one or more light sources (e.g., lasers) to generate light scatter and a fluorescence information. The information for a particle is analyzed such as by sorting electronics or other detection system (not shown in FIG. 2A). The deflection plates 252 and 254 may be independently controlled to attract or repel the charged droplet to guide the droplet toward a destination collection receptacle (e.g., one of 272, 274, 276, or 278). As shown in FIG. 2A, the deflection plates may be controlled to direct a particle along a first path 262 toward the receptacle 274 or along a second path 268 toward the receptacle 278. If the particle is not of interest (e.g., does not exhibit scatter or illumination information within a specified sort range), deflection plates may allow the particle to continue along a flow path 264. Such uncharged droplets may pass into a waste receptacle such as via aspirator 270.

The sorting electronics may be included to initiate collection of measurements, receive fluorescence signals for particles, and determine how to adjust the deflection plates to cause sorting of the particles. Example implementations of the embodiment shown in FIG. 2A include the BD FACSAria™ line of flow cytometers commercially provided by Becton, Dickinson and Company of San Jose, California.

Figure 2B:
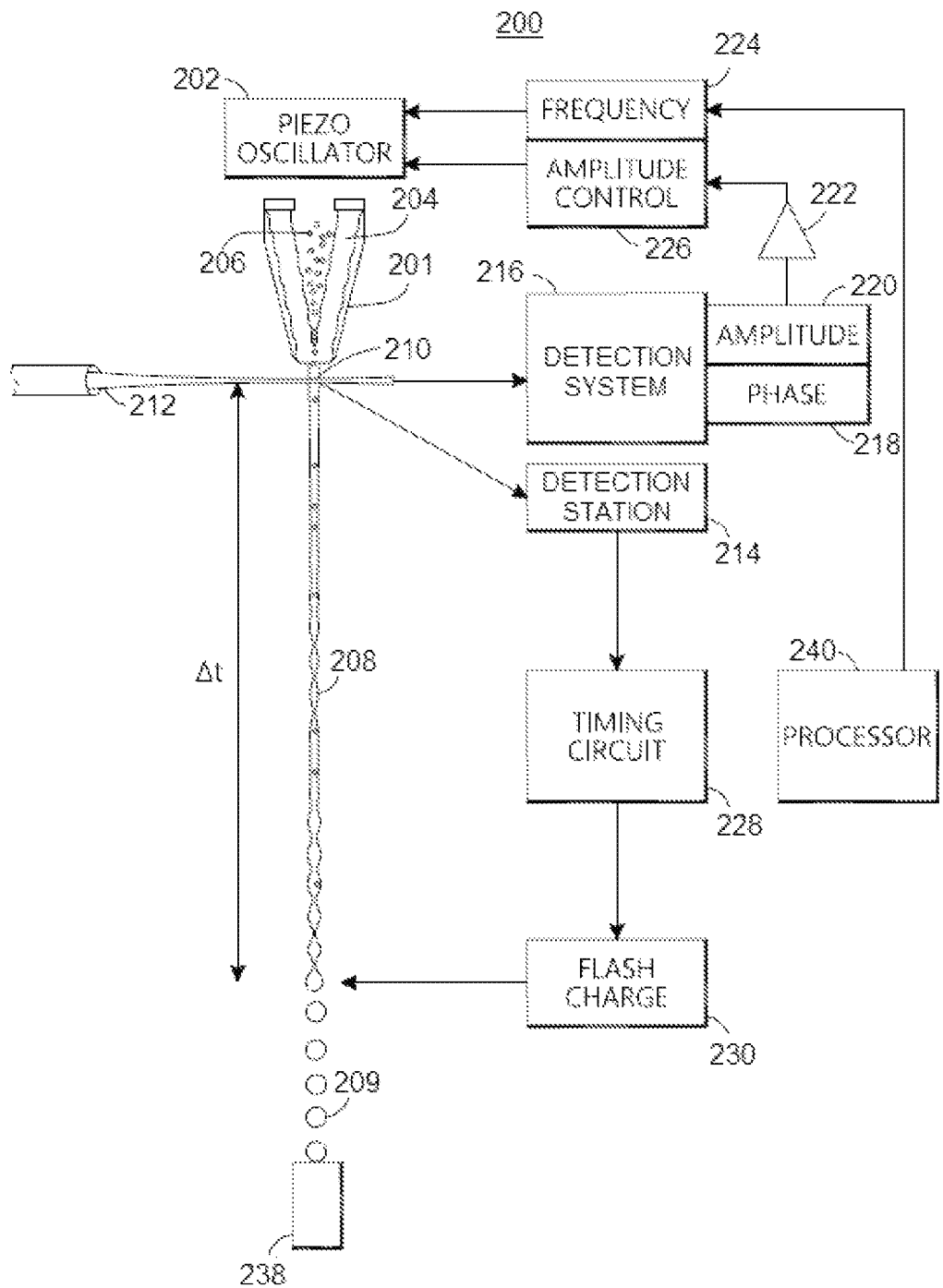
FIG. 2B is a schematic drawing of a particle sorter system 200, in accordance with one embodiment presented herein

FIG. 2B is a schematic drawing of a particle sorter system 200, in accordance with one embodiment presented herein. In some embodiments, the particle sorter system 200 is a cell sorter system. As shown in FIG. 2B, a drop formation transducer 202 (e.g., piezo-oscillator) is coupled to a fluid conduit 201 such as nozzle. Within fluid conduit 201, sheath fluid 204 hydrodynamically focuses a sample fluid 206 into a moving fluid column 208 (e.g. stream). Within the moving fluid column 208, particles (e.g., cells) are lined up in single file to cross a monitored area 210 (e.g., laser-stream intersect), irradiated by an irradiation source 212 (e.g., laser). Vibration of the drop formation transducer 202 causes moving fluid column 208 to break into a plurality of drops 209.

In operation, a detection station 214 (e.g., event detector) identifies when a particle of interest (or cell of interest) crosses monitored area 210. Detection station 214 feeds into timing circuit 228, which in turn feeds into flash charge circuit 230. At a drop break off point, informed by a timed drop delay ($\Delta t$), a flash charge is applied to the moving fluid column 208 such that a drop of interest carries a charge. The drop of interest may include one or more particles or cells to be sorted. The charged drop can then be sorted by activating deflection plates (not shown) to deflect the drop into a vessel such as a collection tube or a multi-well sample plate where a well may be associated with drops of particular interest. As shown in FIG. 2B, however, the drops are collected in a drain receptacle 238.

A detection system 216 (e.g. drop boundary detector) serves to automatically determine the phase of a drop drive signal when a particle of interest passes the monitored area 210. An exemplary drop boundary detector is described in U.S. Pat. No. 7,679,039, which is incorporated herein by reference in its entirety. Detection system 216 allows the instrument to accurately calculate the place of each detected particle in a drop. Detection system 216 may feed into an amplitude signal 220 and/or phase 218 signal, which in turn feeds (via amplifier 222) into an amplitude control circuit 226 and/or frequency control circuit 224. Amplitude control circuit 226 and/or frequency control circuit 224, in turn, controls the drop formation transducer 202. The amplitude control circuit 226 and/or frequency control circuit 224 may be included in a control system.

In some implementations, sort electronics (e.g., the detection system 216, the detection station 214 and a processor 240) may be coupled with a memory configured to store the detected events and a sort decision based thereon. The sort decision may be included in the event data for a particle. In some implementations, the detection system 216 and the detection station 214 may be implemented as a single detection unit or communicatively coupled such that an event measurement may be collected by one of the detection system 216 or the detection station 214 and provided to the non-collecting element.

In some embodiments, one or more components described for the particle sorter system 200 may be used to analyze and characterize particles, with or without physically sorting the particles into collection vessels. Likewise, one or more components described below for the particle analysis system 300 (FIG. 3) may be used to analyze and characterize particles, with or without physically sorting the particles into collection vessels. For example, particles may be grouped or displayed in a tree that includes at least three groups as described herein, using one or more of the components of the particle sorter system 200 or particle analysis system 300.

Figure 3:
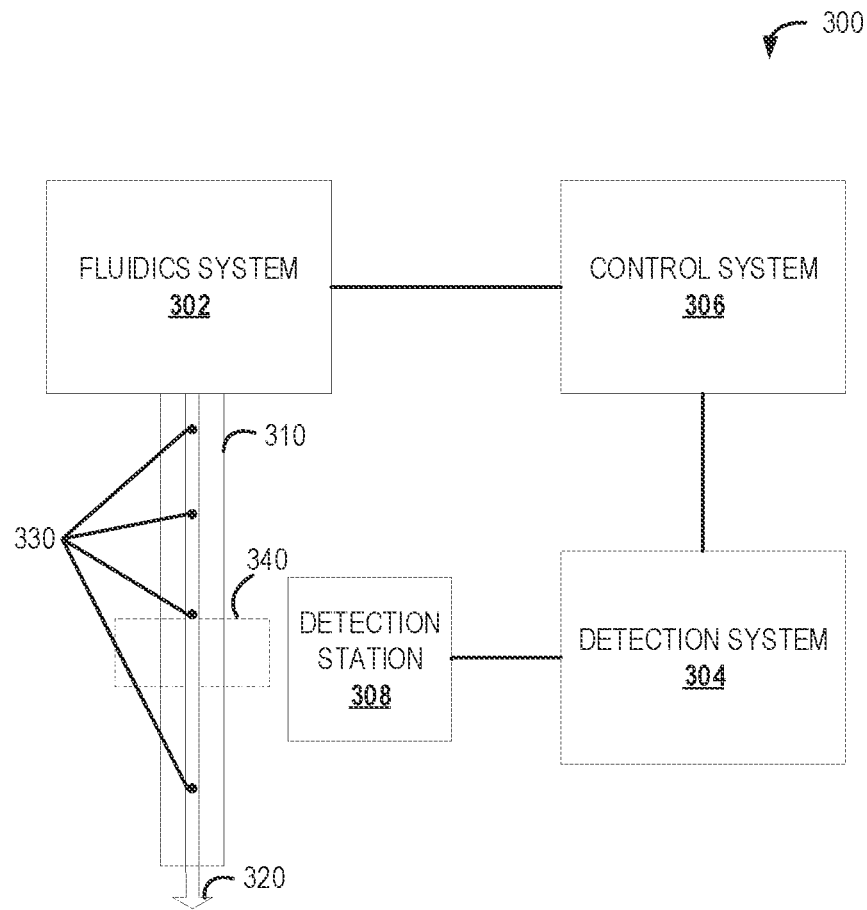
FIG. 3 shows a functional block diagram of a particle analysis system for computational based sample analysis and particle characterization.

FIG. 3 shows a functional block diagram of a particle analysis system for computational based sample analysis and particle characterization. In some embodiments, the particle analysis system 300 is a flow system. The particle analysis system 300 shown in FIG. 3 may be configured to perform, in whole or in part, the methods described herein such as, for example, the method of FIG. 6. The particle analysis system 300 includes a fluidics system 302. The fluidics system 302 may include or be coupled with a sample tube 310 and a moving fluid column within the sample tube in which particles 330 (e.g. cells) of a sample move along a common sample path 320.

The particle analysis system 300 includes a detection system 304 configured to collect a signal from each particle as it passes one or more detection stations along the common sample path. A detection station 308 generally refers to a monitored area 340 of the common sample path. Detection may, in some implementations, include detecting light or one or more other properties of the particles 330 as they pass through a monitored area 340. In FIG. 3, one detection station 308 with one monitored area 340 is shown. Some implementations of the particle analysis system 300 may include multiple detection stations. Furthermore, some detection stations may monitor more than one area.

Each signal is assigned a signal value to form a data point for each particle. As described above, this data may be referred to as event data. The data point may be a multidimensional data point including values for respective properties measured for a particle. The detection system 304 is configured to collect a succession of such data points in a first time interval.

The particle analysis system 300 also includes a control system 306. The control system 306 may include one or more processors, an amplitude control circuit 226 and/or a frequency control circuit 224 as shown in FIG. 2B. The control system 306 shown is operationally associated with the fluidics system 302. The control system 306 configured to generate a calculated signal frequency for at least a portion of the first time interval based on a Poisson distribution and the number of data points collected by the detection system 804 during the first time interval. The control system 306 is further configured to generate an experimental signal frequency based on the number of data points in the portion of the first time interval. The control system 306 additionally compares the experimental signal frequency with that of a calculated signal frequency or a predetermined signal frequency.

Figure 4:
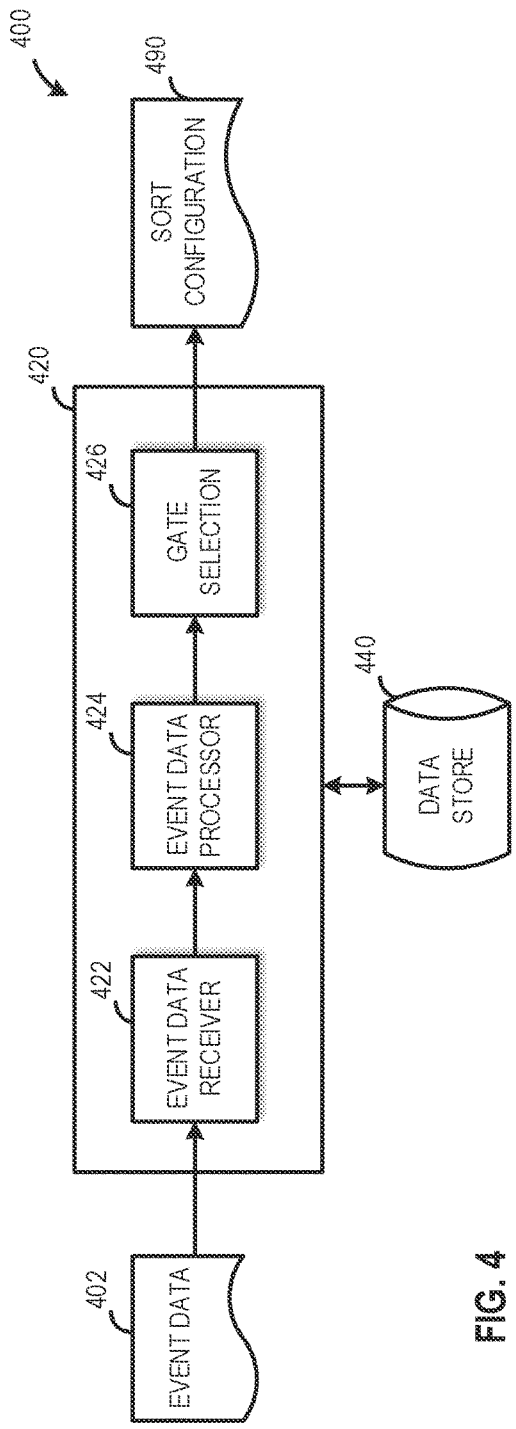
FIG. 4 is a diagram showing an example system to dynamically transform event data.

FIG. 4 is a diagram showing an example event selection system to dynamically identify event data such as for generating a sorting configuration. The event selection system 400 includes a selection device 420. The selection device 420 includes an event data receiver 422. The event data receiver 422 may receive event data 402 from a particle analyzer such as the particle analyzer 102 shown in FIG. 1. In some implementations, the event data 402 may be generated by a particle analyzer by received from, for example, an analytics workstation. For example, a user may provide the event data 402 which was obtained from a particle analyzer to the event data receiver 422. The event data receiver 422 may include a transceiver for wireless communication or a port for connecting to a wired network such as an Ethernet local area network or device such as via a Universal Serial Bus or THUNDERBOLT® connection.

The event data receiver 422 may provide at least a portion of the event data 402 to event data processor 424 included in the selection device 420. The event data processor 424 may identify a transformation to apply for the event data. The identification may include detecting a value in the event data such as an identifier for the assay or experiment. The available transformations may be stored in a data store 440 accessible by the event data processor 424. The transformation of the event data performed by the event data processor 424 may be a parametric or non-parametric transformation. In some implementations, the transformation may be specified by a device providing the event data 402. For example, an analysis workstation may submit a message requesting processing of the event data 402. The message may include a desired transformation (e.g., tSNE). In some implementations, the event data processing may be guided based on a user input. For example, the user may identify a transform to apply to the received event data.

The selection device 420 may include a gate selection 426 unit. The gate selection 426 unit may receive, from an input device, a selection of events of interest. The selection may be referred to as a gate. The selection may define one or more ranges of parameter values for events of interest. The one or more ranges may be used by the gate selection 426 unit to generate a classifier or other sort configuration 490. The sort configuration 490 may be represented as a truth table or decision tree to identify those events associated with the gate. As discussed, the manual acquisition of a gate can be fraught with error and, in some instances, overlook significant parameters or potential hardware bottlenecks or efficiencies. Accordingly, the initial selection may be used as an example of the desired sort which can be adapted through further processing, without manual intervention, to optimize the search strategy.

Figure 5:
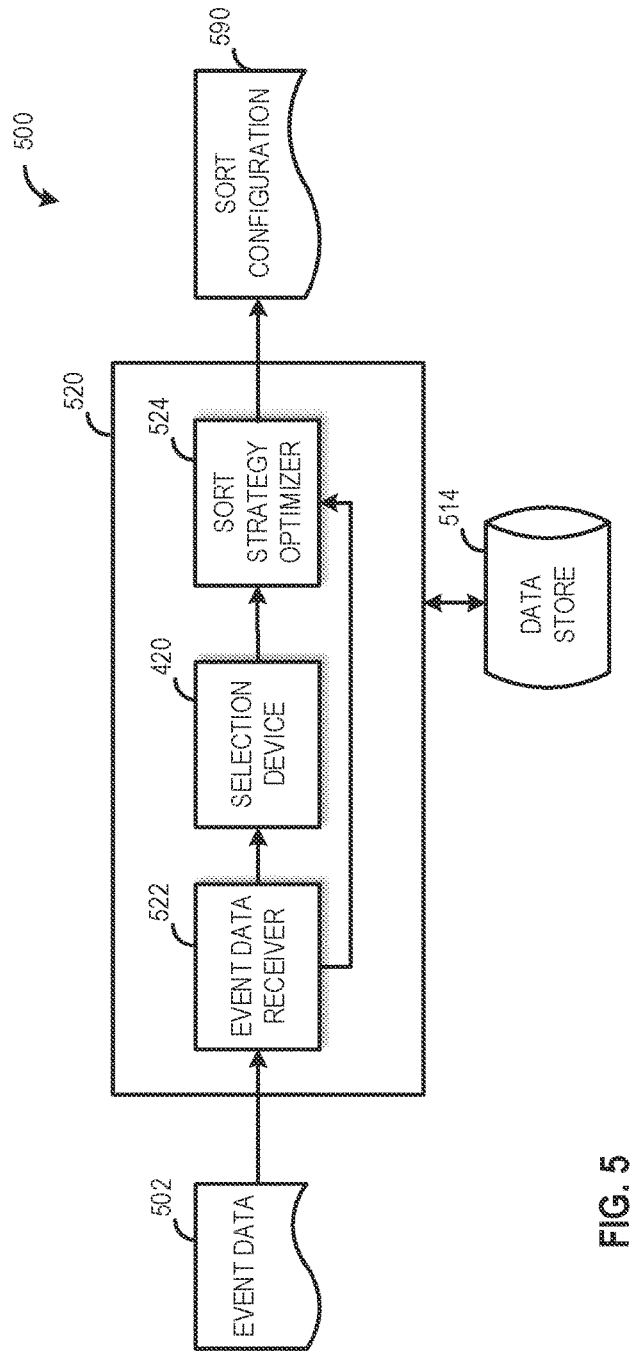
FIG. 5 is a diagram showing an example system to dynamically transform event data using a parametric machine learning transformation.

FIG. 5 is a diagram showing an example system for adaptive generation of a sort configuration. The adaptive sorting device 520 in FIG. 5 includes features to receive a selection from a selection device, such as the selection device 420, and then generate an optimized search strategy for assessing events.

The system 500 includes an adaptive sorting device 520. The adaptive sorting device 520 includes an event data receiver 522. The event data receiver 522 may receive event data 502 from a particle analyzer such as the particle analyzer 102 shown in FIG. 1. In some implementations, the event data 502 may be generated by a particle analyzer by received from, for example, an analytics workstation. For example, a user may provide the event data 502 which was obtained from a particle analyzer to the event data receiver 522. The event data receiver 522 may include a transceiver for wireless communication or a network port for connecting to a wired network such as an Ethernet local area network.

The event data receiver 522 may provide at least a portion of the event data 502 to the selection device 420. The selection device 420 may acquire an example sort configuration from a user. The example along with the received event data 502 may be provided to a sort strategy optimizer 524. The sort strategy optimizer 524 may iteratively generate a sort strategy that approximates the example sort configuration. A sort strategy may include a dynamic pipeline of event data transformations or selections. The available transformations or sorting steps may be stored in a data store 514 accessible by the sort strategy optimizer 524. Candidate strategies may include may include automatically detecting populations and scoring each event against relevant target and off-target populations (computational sort). The strategies may include approximation of transforms (non-parametric and parametric) using neural networks or other machine learning techniques. The strategies may include projecting target populations from a parameter space that is not sortable to one that is. As part of projecting the target populations, the system may identify computable parameters that, in combination, approximate parameters that are not easily computable. The strategies may include automatically extracting features from images or high-dimensional measurements including, for example, time series waveform data. One example of the automatic feature extraction is an auto-encoder neural network to learn relevant image features to be used in sorting decisions.

In some implementations, neural networks may be used for both feature generation and gating strategy generation. For feature generation, neural networks that receive raw image data as input and output metrics of what images "look" like. Other neural networks such as those that receive computed parameters (e.g., pulse area or height) as inputs and output new parameters. These new parameters provide a projection from the original parameter space to a new parameter space. For gating strategy generation, neural networks that receive a variety of parameters as input and output a single value which can be used for a sorting decision may be trained or used to generate a sorting decision.

Figure 6:
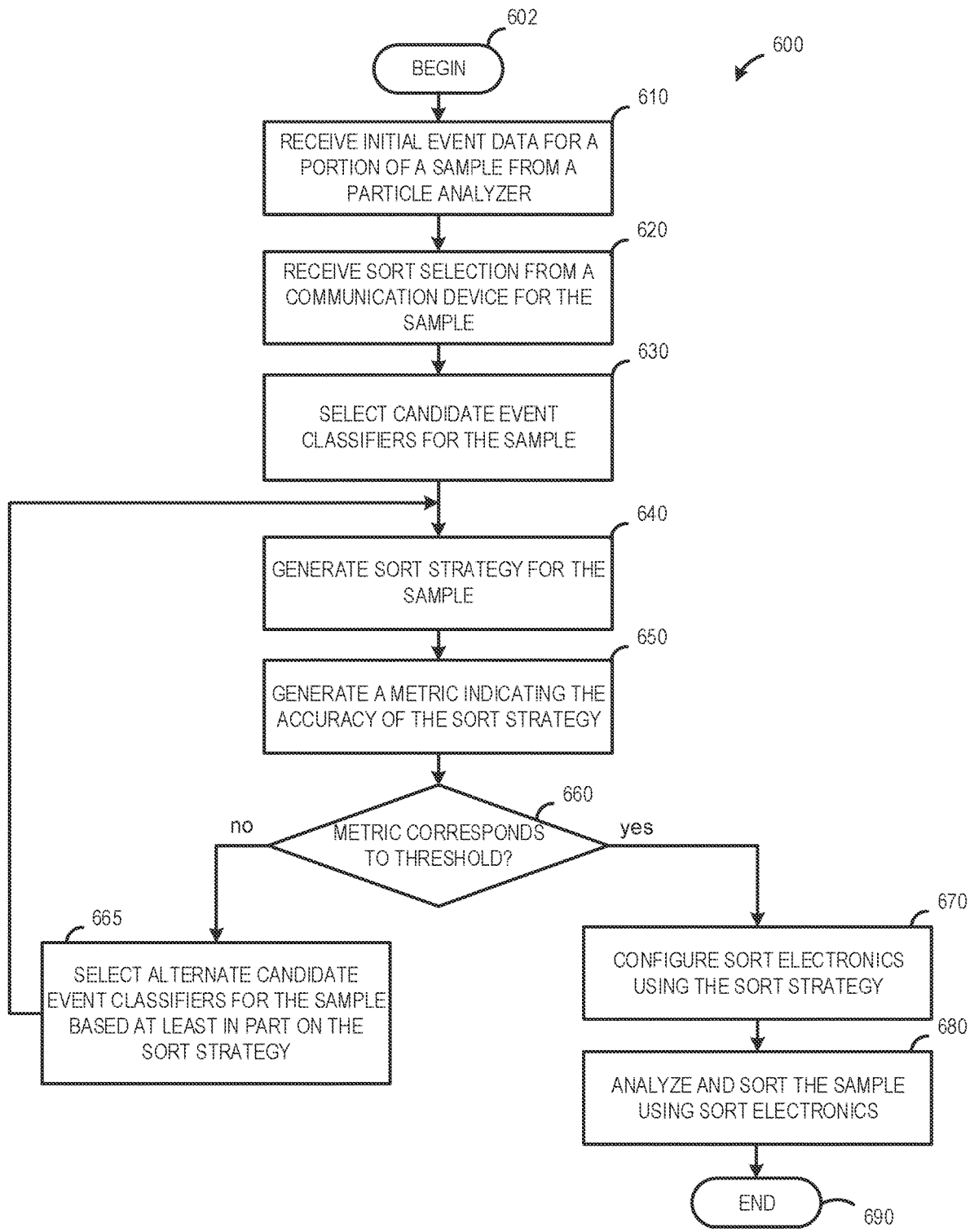
FIG. 6 is a process flow diagram depicting an example of a method of parametric machine learning transformation for multi-dimensional event data.

FIG. 6 is a process flow diagram depicting an example of a method of adaptive generation of an optimized sort strategy. The method 600 may be implemented in whole or in part by an adaptive sorting device, such as the adaptive sorting device 520 shown in FIG. 5.

The method 600 begins at block 602. At block 610, initial event data for a portion of a sample may be received. The event data may be collected after activating a particle analyzer to process the portion of the sample. Processing the sample may include measuring a property of particles such as graphic, electrical, temporal, or acoustic properties. In some implementations, the collection of the initial event data may be omitted and the method 600 may proceed from block 602 to block 620. This may be desirable in instances where the size of the sample is small. In such cases, to preserve the amount of sample available for sorting, the sort configuration may be assessed without consuming any of the sample.

At block 620, a sort selection for the sample is received from a communication device. The sort selection may represent an example of the population of events to be sorted. The sort selection may include a gate, an example image, or an example event. The sort selection may be identified relative to the event data for an initial portion of the sample received at block 610. For example, the researcher may draw a polygon on a graph of event data measurements to define a range of data values to be sorted. The polygon may define a gate which can be or be associated with a sort criteria.

The sort selection may serve as a reference for developing an optimized sort configuration. In some implementations, the sort selection may include information identifying the target sorting instrument or sort electronics. As discussed, different hardware may have different capabilities to implement a sort configuration. To ensure the sort configuration is adapted for the target hardware, the identity of the instrument may be considered.

At block 630, candidate event classifiers for the sample may be identified. The identification may include selecting event classifiers from a data store. The event classifiers may include neural network models, event data transformations, autoencoders, or other machine implemented elements for assessing event data. The selection may be based in part on a type of sample (e.g., blood, urine, tissue, etc.). The selection may be based in part on the particle analyzer that will be used to process the sample. The selection may be based in part on the sort selection received from the communication device. For example, if the sort selection includes an image, a graphics based classifier may be selected as a candidate event classifier. As another example, if the distribution of events in the sort selection features a statistically regular distribution, it may be desirable to use a Mahalanobis-based classifier.

In some implementations, a user interface may be provided to collect information specifying which classifiers to include in the candidate event classifiers. In some implementations, the system may consider the set of parameters and classifiers defined in a data store. The classifiers may be filtered based on, for example, how the sample events were identified by the user. As classifiers are identified, historical identification information may be used to identify common workflows that bundle together classifiers and parameters that are selected together for an experiment, target particle, particle analyzer generating the data, or other detectable property of an experiment or of the data generated during the experiment.

At block 640, a sort strategy may be generated using one or more of the candidate event classifiers. Generating a sort strategy may include sequencing one or more of the candidate event classifiers to form a pipeline for processing event data. Generating the sort strategy may include using the user's example gating strategy to inform how different classifiers and/or parameters should be linked together. For instance, if the user arrives at their example population using hierarchal gates then we can use a similar hierarchal structure. Another example would be if users used a transformed space at any point in determining their example data, the system may detect the transformation and generate an approximation of that transformation for the sort strategy. Yet another example is detecting high numbers of hierarchal gates as an attempt to draw manifolds in high dimensional spaces and employ tools like relationship preserving transformations or statistical models like Mahalanobis distance.

As sort strategies are identified, historical strategy information may be used to identify common workflows that sequence particular identifiers for an experiment, target particle, particle analyzer generating the data, or other detectable property of an experiment or of the data generated during the experiment.

The sort strategy generated at block 640 may be assessed using a metric. At block 650, a metric indicating the accuracy of the sort strategy is generated. The metric may represent the accuracy (e.g., purity) of the sorted events from the sample. The metric may be generated based on a confidence of the classifiers included in the sort strategy. In some implementations, the metric may be generated based on a comparison of the sort selection with the sorting configuration generated by the sort strategy. One way the metric may be generated is using an F-measure for the sort strategy whereby the precision indicates a level of sort purity and the recall indicates a quantity or yield of the sorted sample. For example, the example events provided by a user can be divided into "training" and "testing" subsets. The division may be based on pseudorandom selection of a portion of the events. The training subset may be used to train a number of candidate gating strategies. These gating strategies can then be used to evaluate the testing subset. The results of this test will be used to generate an F-measure.

At block 660, a determination is made as to whether the metric for the sort strategy corresponds to a threshold. The threshold may be a predetermined configuration value indicating a minimum purity or yield for a sort strategy. If the determination at block 660 is affirmative, the generated sort strategy may be deemed adequate for the sample. In such instance, the method 600 proceeds to block 670.

At block 670, sort electronics (e.g., sorting circuitry) may be configured using the sort strategy generated at block 640. The configuration of the sort electronics may include storing a model or transformation included in the strategy in a memory location accessible to the sort electronics. The sort strategy may then be used to process event data for assessment against sorting criteria included in the sort strategy.

At block 680, the analyzer may assess and sort remaining portion(s) of the sample using the configured sort electronics. As a new event measurement is collected, the measurement may be processed, in real time, using the configured sort electronics and sorted to the specified vessel according to the sort configuration. For example, the deflection plates of the particle analyzer may be activated to direct a particle of interest into a specified collection tube.

The method 600 may end at block 690. However, it will be appreciated that the method 600 may be repeated for additional events, samples, or experiments. In some implementations, it may be desirable to generate a new sort strategy to adapt to any variations within the sample or to account for a change in the sample source. For example, in a therapeutic environment, a biological sample may be collected during administration of a drug or other compound. The sort strategy may need adjusting to account for the presence of the drug or compound once administered or unanticipated variation from the initial example selection used to guide the generation of the adaptive strategy. In such instances, the sort strategy may be regenerated in part based on data collected since the original search strategy was trained. For example, the initial strategy may have identified a normal distribution of events, but the actual event data collected for the sample may indicate events having a non-normal distribution.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields, buttons, or other interactive controls for receiving input signals or providing electronic information or for providing information to the user in response to any received input signals. A UI may be implemented in whole or in part using technologies such as hyper-text mark-up language (HTML), JAVASCRIPT™, FLASH™, JAVA™, .NET™, WINDOWS OS™, macOS™, web services, or rich site summary (RSS). In some implementations, a UI may be included in a stand-alone client (for example, thick client, fat client) configured to communicate (e.g., send or receive data) in accordance with one or more of the aspects described.

As used herein a "data store" may be embodied in hard disk drives, solid state memories and/or any other type of non-transitory computer-readable storage medium accessible to or by a device such as an access device, server, or other computing device described. A data store may also or alternatively be distributed or partitioned across multiple local and/or remote storage devices as is known in the art without departing from the scope of the present disclosure. In yet other embodiments, a data store may include or be embodied in a data storage web service.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed adaptive sort strategy processor, which may include one or more processors, such as one or more digital signal processors (DSPs), configurable microprocessors, an application specific integrated circuits (ASICs), field programmable gate arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. In some aspects, the functionality described herein may be provided within dedicated software modules or hardware modules configured for encoding and decoding, or incorporated in a specialized sorting control card.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following illustrative claims.

The invention claimed is:

1. A computer-implemented method comprising:
    under control of one or more processing devices,
        receiving, from a communication device, a reference sorting criteria for a sample with a particle analyzer;
        identifying candidate event classifiers for the sample based at least in part on the reference sorting criteria, the sample or both;
        generating a sorting strategy based at least in part on one or more of the candidate event classifiers; and
        configuring the particle analyzer to classify a particle for the sample based at least in part on the sorting strategy, a multidimensional measurement for the particle and the sorting strategy; or both.

2. The computer-implemented method of claim 1, wherein the reference sorting criteria comprises gate information identifying a range of measurements for classifying the particle.

3. The computer-implemented method of claim 1, wherein the reference sorting criteria comprises an image showing a reference particle to be collected from the sample.

4. The computer-implemented method of claim 1, further comprising:
    transmitting a sorter configuration to the particle analyzer, wherein the sorter configuration represents the sorting strategy; and
    adjusting sorting circuitry based at least in part on the sorter configuration.

5. The computer-implemented method of claim 4, wherein the sorting circuitry comprises a field programmable gate array.

6. The computer-implemented method of claim 1, wherein the multidimensional measurement comprises a measurement of light emitted fluorescently by the particle.

7. The computer-implemented method of claim 6, wherein the light emitted fluorescently by the particle comprises light emitted fluorescently by antibodies bound to the particle.

8. The computer-implemented method of claim 1, further comprising generating a metric indicating an accuracy of the sorting strategy.

9. The computer-implemented method of claim 8, wherein the metric comprises an f-measure of the sorting strategy, wherein a precision component of the f-measure represents purity for sorting of the sample according to the sorting strategy, and wherein a recall component of the f-measure represents yield for sorting of the sample according to the sorting strategy.

10. The computer-implemented method of claim 1, further comprising:
    storing, in a data store, the candidate event classifiers, wherein the candidate event classifiers comprise at least two of:
        (a) a computational sorting classifier including: a scoring and relevant target or off-target score, wherein a score for a particle measurement is compared with the relevant target or off-target score for sorting;

(b) a transformation to convert one or more measurements for a particle into an approximate measurement for the particle;

(c) a parameter projection to convert a population represented by the reference sorting criteria from a first parameter space that is not sortable into a second parameter space that can be sorted; and (d) a feature extraction to generate a vector features from images or high-dimensional measurements, wherein the vector of features are used to classify a particle.

11. The computer-implemented method of claim 1, further comprising:

receiving, from the particle analyzer, a hardware identifier indicating sorting circuitry implemented in the particle analyzer, wherein identifying the candidate event classifiers is further based at least in part on the hardware identifier.

12. A non-transitory computer-readable medium having stored thereon instructions which when executed perform the method of claim 1.

13. An apparatus comprising a processor, wherein the processor is configured to perform the method of claim 1.

14. A system comprising:
a particle analyzer;
a communication device;
one or more processing devices; and
a computer-readable storage medium comprising instructions that, when executed by the one or more processing devices, causes the system to,
receive, from the communication device, a reference sorting criteria;
identify candidate event classifiers for the sample based at least in part on the reference sorting criteria;
generate a sorting strategy based at least in part on one or more of the candidate event classifiers; and
generate an operational adjustment based at least in part on the sorting strategy.

15. The system of claim 14,
wherein the system further comprises sorting electronics communicatively coupled to a deflection plate,
wherein the particle analyzer is further configured to identify a target vessel for a particle based at least in part on a measurement corresponding the sorting strategy for the target vessel, and
wherein the operational adjustment comprises application of a charge via a deflector plate to direct the particle into a target vessel.

16. The system of claim 14, where the particle analyzer further comprises a fluidics system, and wherein the operational adjustment comprises regulating a pressure applied during an experiment for analyzing a sample.

* * * * *